United States Patent

Maurer et al.

[11] Patent Number: 4,503,057
[45] Date of Patent: Mar. 5, 1985

[54] COMBATING PESTS WITH NOVEL SUBSTITUTED N,N-DIMETHYL O-PYRIMIDIN-4-YL CARBAMATES

[75] Inventors: Fritz Maurer, Wuppertal; Ingeborg Hammann, Muelheim; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 474,402

[22] Filed: Mar. 11, 1983

[30] Foreign Application Priority Data

Mar. 25, 1982 [DE] Fed. Rep. of Germany ........ 3211035

[51] Int. Cl.³ .................... C07D 239/34; A01N 47/18
[52] U.S. Cl. .................... 514/269; 544/253; 544/319
[58] Field of Search ............... 424/251; 544/319, 253

[56] References Cited

FOREIGN PATENT DOCUMENTS 0002200 8/1979 European Pat. Off. .
0008762 3/1980 European Pat. Off. .
0022511 1/1981 European Pat. Off. .

Primary Examiner—Robert Gerstl
Attorney, Agent, or Firm—Sprung, Horn, Kramer & Woods

[57] ABSTRACT

Substituted N,N-dimethyl O-pyrimidin-4-yl carbamates of the formula

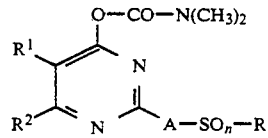

in which
R is alkyl,
$R^1$ is hydrogen or optionally substituted alkyl, alkoxy, alkylthio, alkylsulphinyl or alkylsulphonyl,
$R^2$ is hydrogen or optionally substituted alkyl, or
$R^1$ and $R^2$ together form an optionally substituted alkylene,
A is alkylene having more than 1 carbon atom, and
n is 0, 1 or 2, which possess insecticidal activity.

10 Claims, No Drawings

COMBATING PESTS WITH NOVEL SUBSTITUTED N,N-DIMETHYL O-PYRIMIDIN-4-YL CARBAMATES

The invention relates to new substituted N,N-dimethyl O-pyrimidin-4-yl carbamates, several processes for their preparation, and their use as pest-combating agents, in particular as insecticides.

It is known that certain N,N-dialkyl O-pyrimidinyl carbamates, such as, for example, N,N-dimethyl O-(2-isopropyl-6-methyl-pyrimidin-4-yl)carbamate and N,N-dimethyl O-(2-methylthio-6-methylpyrimidin-4-yl)carbamate, possess insecticidal properties (see French Patent Specification No. 1,443,910 and U.S. Pat. No. 2,694,712).

However, the insecticidal action of these compounds, in particular in the case of low active compound combinations and use amounts, is not always satisfactory.

The following have been found:

(1) Substituted N,N-dimethyl O-pyrimidin-4-yl carbamates of the formula I

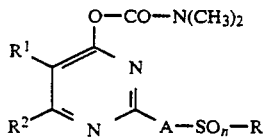

in which
R represents alkyl,
$R^1$ represents hydrogen, or represents optionally substituted radicals from the series comprising alkyl, alkoxy, alkylthio, alkylsulphinyl or alkylsulphonyl,
$R^2$ represents hydrogen or optionally substituted alkyl, or
$R^1$ and $R^2$ together represent optionally substituted alkylene,
A represents straight-chain or branched alkylene having more than 1 C atom, and
n represents 0, 1 or 2.

(2) Process for the preparation of the new substituted N,N-dimethyl O-pyrimidin-4-yl carbamates of the formula

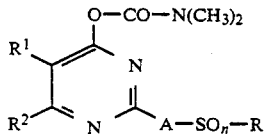

in which
R represents alkyl,
$R^1$ represents hydrogen, or represents optionally substituted radicals from the series comprising alkyl, alkoxy, alkylthio, alkylsulphinyl or alkylsulphonyl,
$R^2$ represents hydrogen or optionally substituted alkyl, or
$R^1$ and $R^2$ together represent optionally substituted alkylene,
A represents straight-chain or branched alkylene having more than 1 C atom, and
n represents 0, 1 or 2,
characterized in that
(a) hydroxy-pyrimidines of the formula II

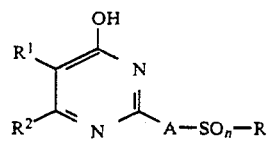

in which
R, $R^1$, $R^2$, A and n have the meanings given above, are reacted with N,N-dimethyl-carbamic acid-halides of the formula III

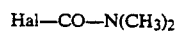

in which Hal represents chlorine or bromine, if appropriate in the presence of an acid acceptor and if appropriate with the use of a diluent; or (b) hydroxy-pyrimidines of the formula (II), in which R, $R^1$, $R^2$, A and n have the meanings given above, are reacted with phosgene and then with dimethylamine, if appropriate in the presence of an acid acceptor and if appropriate with the use of a diluent;

(c) compounds of the formula (I), in which
n represents 1 or 2, and/or
$R^1$ represents alkylsulphinyl or alkylsulphonyl, are also obtained by reacting compounds of the formula (I), in which
n represents 0, and/or
$R^1$ represents alkylthio,
with oxidizing agents, if appropriate in the presence of a diluent; or (d) N,N-dimethyl O-pyrimidin-4-yl carbamates of the formula IV

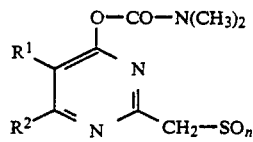

in which $R^1$, $R^2$, R and n have the meanings given above, are reacted with alkyl halides of the formula V

in which
$R^3$ represents alkyl and
Hal represents chlorine, bromine or iodine, if appropriate in the presence of acid acceptors and if appropriate in the presence of diluents.

(3) New hydroxypyrimidines of the formula II

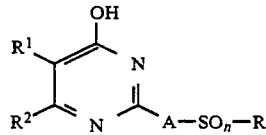

in which A, R, $R^1$, $R^2$ and n have the meanings given above.

(4) Process for the preparation of the new hydroxypyrimidines of the formula II, characterized in that acetates of the formula VI

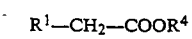

in which
R¹ has the meaning given above and
R⁴ represents alkyl having 1–4 C atoms,
are reacted with esters of the formula VII $$R^2—COOR^5 \qquad (VII)$$

in which
R² has the meaning given above and
R⁵ represents alkyl having 1–4 C atoms,
and with amidines of the formula VIII

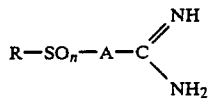

(VIII)

in which R, A and n have the meanings given above, or their hydrohalides, if appropriate in the presence of acid acceptors and if appropriate in the presence of diluents.

The new substituted N,N-dimethyl O-pyrimidin-4-yl carbamates of the formula (I) are distinguished by high activity as pest-combating agents, in particular by outstanding insecticidal action.

Surprisingly, the substituted N,N-dimethyl O-pyrimidin-4-yl carbamates according to the invention show a substantially greater insecticidal action than the compounds, such as, for example, N,N-dimethyl O-(2-isopropyl-6-methyl-pyrimidin-4-yl)carbamate and N,N-dimethyl O-(2-methylthio-6-methyl-pyrimidin-4-yl)carbamate, which are known from the prior art and are compounds of analogous constitution and identical direction of action.

The invention preferably relates to compounds of the formula (I), in which

R represents alkyl having 1 to 6 carbon atoms,

R¹ represents hydrogen or represents alkyl, alkoxy, alkylthio, alkylsulphinyl or alkylsulphonyl, each of which have 1 to 6 carbon atoms, which can be optionally substituted by halogen, C₁₋₂-alkoxy or C₁₋₂-alkylthio, R² represents hydrogen or alkyl which has 1 to 6 carbon atoms and can be optionally substituted by halogen, in particular chlorine or fluorine, or by C₁₋₂-alkoxy or C₁₋₂-alkylthio, or R¹ and R² together represent alkylene which has 2 to 4 carbon atoms and can be optionally substituted by halogen, in particular chlorine, or by C₁₋₂-alkyl or C₁₋₂-alkylthio, A represents straight-chain or branched alkylene having 2 to 6 carbon atoms, and n represents 0, 1 or 2.

Particularly preferred compounds of the formula (I) are those in which

R represents methyl, ethyl, n-propyl, i-propyl, n-butyl, i-butyl, sec.-butyl and tert.-butyl, R¹ represents hydrogen, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, n-propylthio, i-propylthio, n-butylthio, i-butylthio, sec.-butylthio, tert.-butylthio, methyl-, ethyl-, n-propyl-, i-propyl-, n-butyl-, i-butyl-, sec.-butyl- and tert.-butylsulphinyl or sulphonyl, R² represents hydrogen, methyl, ethyl, n-propyl, i-propyl, n-butyl, i-butyl, sec.-butyl and tert.-butyl, or R¹ and R² together represent alkylene having 2 to 4 carbon atoms, A represents straight-chain or branched alkylene having 2 to 6 carbon atoms, and n represents 0, 1 or 2.

If, for example, N,N-dimethyl-carbamic acid chloride is used in process (a), phosgene and dimethylamine are used in process (b) and 2-(2-methylsulphonylethyl)-5,6-dimethyl-4-hydroxy-pyrimidine is used in both the processes as starting materials, the corresponding reactions can be represented by the following equations:

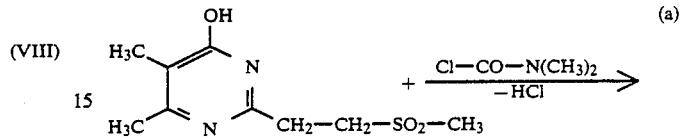

(a)

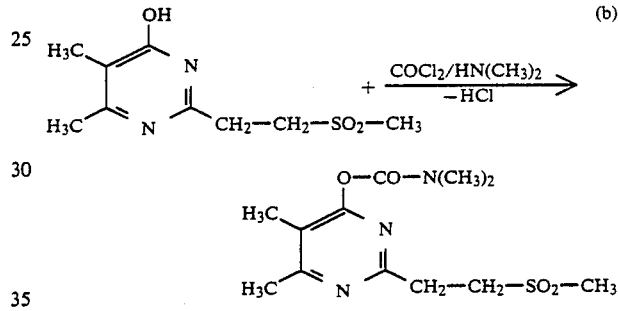

(b)

If, for example, N,N-dimethyl O-(2-(2-methylthioethyl)-5,6-dimethyl-pyrimidin-4-yl)carbamate and hydrogen peroxide are used as starting materials in process (c), the corresponding reaction can be represented by the following equation:

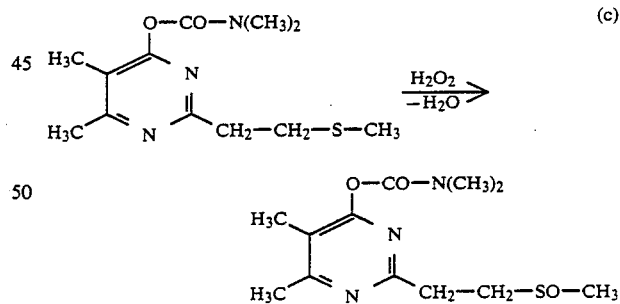

(c)

If, for example, N,N-dimethyl O-(2-(-methylsulphonylmethyl)-5-methoxy-6-methyl-pyrimidin-4-yl)carbamate and methyl iodide are used as starting materials in process (d), the corresponding reaction can be represented by the following equation:

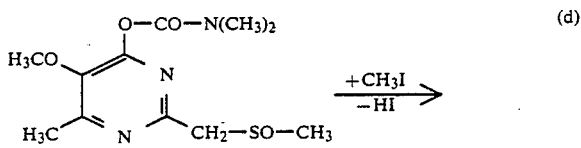

(d)

-continued

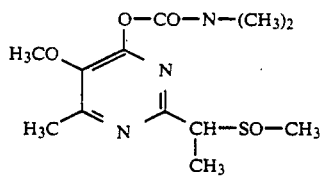
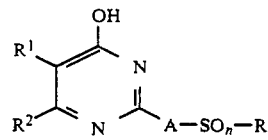

TABLE 1

| $R^1$ | $R^2$ | R | A | n |
|---|---|---|---|---|
| $CH_3$ | $CH_3$ | $CH_3$ | $-CH_2-CH_2-$ | 0 |
| $CH_3$ | $CH_3$ | $CH_3$ | $-CH_2-CH_2-$ | 1 |
| $CH_3$ | $CH_3$ | $CH_3$ | $-CH_2-CH_2-$ | 2 |
| $CH_3$ | $CH_3$ | $CH_3$ | $-CH(CH_3)-$ | 2 |
| $-CH_2-CH_2-CH_2-$ | | $CH_3$ | $-CH(CH_3)-$ | 2 |
| $-CH_2-CH_2-CH_2-$ | | $CH_3$ | $-CH(C_2H_5)-$ | 2 |
| $-CH_2-CH_2-CH_2-$ | | $CH_3$ | $-CH_2-CH_2-$ | 0 |
| $-OCH_3$ | H | $CH_3$ | $-CH_2-CH_2-$ | 0 |
| $CH_3$ | $CH_3$ | $CH_3$ | $-CH(CH_3)-$ | 0 |
| $-OCH_3$ | H | $CH_3$ | $-CH(CH_3)-$ | 0 |
| $-CH_2-CH_2-CH_2-$ | | $CH_3$ | $-CH(CH_3)-$ | 0 |
| $CH_3$ | $CH_3$ | $CH_3$ | $-CH(CH_3)-$ | 1 |
| $-OCH_3$ | H | $CH_3$ | $-CH(CH_3)-$ | 1 |
| $-OCH_3$ | H | $CH_3$ | $-CH(CH_3)-$ | 2 |
| $-CH_2-CH_2-CH_2-$ | | $CH_3$ | $-CH(CH_3)-$ | 1 |
| $-OC_2H_5$ | H | $CH_3$ | $-CH(CH_3)-$ | 0 |
| $-OC_2H_5$ | H | $CH_3$ | $-CH(CH_3)-$ | 1 |
| $-OC_2H_5$ | H | $CH_3$ | $-CH(CH_3)-$ | 2 |
| $-OCH_3$ | H | $CH_3$ | $-CH_2-CH_2-$ | 1 |
| $-OCH_3$ | H | $CH_3$ | $-CH_2-CH_2-$ | 2 |
| $-O-i-C_3H_7$ | H | $CH_3$ | $-CH_2-CH_2-$ | 0 |
| $-OC_2H_5$ | H | $CH_3$ | $-CH_2-CH_2-$ | 0 |
| $CH_3$ | $CH_3$ | $C_2H_5$ | $-CH_2-CH_2-$ | 0 |
| $-OCH_3$ | H | $C_2H_5$ | $-CH_2-CH_2-$ | 0 |
| $CH_3$ | $CH_3$ | $n-C_3H_7$ | $-CH_2-CH_2-$ | 0 |
| $-O-n-C_3H_7$ | H | $CH_3$ | $-CH(CH_3)-$ | 0 |
| $-O-n-C_3H_7$ | H | $CH_3$ | $-CH_2-CH_2-$ | 0 |
| $-O-n-C_3H_7$ | H | $CH_3$ | $-C(CH_3)_2-CH_2-$ | 0 |
| $-O-n-C_3H_7$ | H | $CH_3$ | $-CH(CH_3)-CH_2-$ | 0 |
| $-OCH_3$ | H | $n-C_3H_7$ | $-CH_2-CH_2-$ | 0 |
| $CH_3$ | $CH_3$ | tert.-$C_4H_9$ | $-CH_2-CH_2-$ | 0 |
| $-OCH_3$ | H | tert.-$C_4H_9$ | $-CH_2-CH_2-$ | 0 |
| $-OCH_3$ | H | $CH_3$ | $-CH_2-CH_2-CH_2-$ | 0 |
| $-OCH_3$ | H | $CH_3$ | $-CH_2-CH_2-CH_2-$ | 1 |
| $-OCH_3$ | H | $CH_3$ | $-CH_2-CH_2-CH_2-$ | 2 |
| $CH_3$ | H | $CH_3$ | $-CH_2-CH_2-$ | 0 |
| $CH_3$ | H | $CH_3$ | $-CH(CH_3)-$ | 0 |
| $C_2H_5$ | H | $CH_3$ | $-CH_2-CH_2-$ | 0 |
| $C_2H_5$ | H | $CH_3$ | $-CH(CH_3)-$ | 0 |
| $i-C_3H_7$ | H | $CH_3$ | $-CH_2-CH_2-$ | 0 |
| $i-C_3H_7$ | H | $CH_3$ | $-CH(CH_3)-$ | 0 |
| H | $CH_3$ | $CH_3$ | $-CH_2-CH_2-$ | 0 |
| $-OC_2H_5$ | H | $CH_3$ | $-CH_2-CH_2-$ | 1 |
| $-OC_2H_5$ | H | $CH_3$ | $-CH_2-CH_2-$ | 2 |
| $-SCH_3$ | H | $CH_3$ | $-CH_2-CH_2-$ | 0 |
| $-SCH_3$ | H | $CH_3$ | $-CH(CH_3)-$ | .0 |
| $-OCH_3$ | H | $CH_3$ | $-C(CH_3)_2-CH_2-$ | 0 |
| $CH_3$ | $CH_3$ | $CH_3$ | $-C(CH_3)_2-CH_2$ | 0 |
| $-OCH_3$ | H | $CH_3$ | $-C(CH_3)_2-$ | 0 |
| $CH_3$ | $CH_3$ | $CH_3$ | $-C(CH_3)_2-$ | 0 |
| $-OCH_3$ | H | $CH_3$ | $-C(CH_3)_2-$ | 1 |
| $-OCH_3$ | H | $CH_3$ | $-C(CH_3)_2-$ | 2 |
| $CH_3$ | $CH_3$ | $CH_3$ | $-C(CH_3)_2-$ | 1 |
| $CH_3$ | $CH_3$ | $CH_3$ | $-C(CH_3)_2-$ | 2 |
| $OCH_3$ | H | $CH_3$ | $-CH(CH_3)-CH_2-$ | 0 |
| $CH_3$ | $CH_3$ | $CH_3$ | $-CH(CH_3)-CH_2-$ | 0 |
| H | tert.-$C_4H_9$ | $CH_3$ | $-CH_2-CH_2-$ | 0 |

Formula (II) gives a definition of the hydroxypyrimidines to be used as starting materials in processes (a) and (b). In this formula, R, $R^1$, $R^2$, A and n preferably represent those radicals or indices which have been mentioned in the definition of the radicals or indices in formula (I) as being preferred.

The following may be mentioned as examples of compounds of the formula (II):

The hydroxy-pyrimidines of the formula (II) have not yet been described in the literature. These compounds are obtained by reacting acetates, of the formula (VI), for example methyl methoxy acetate, with esters, of the formula (VII), such as, for example, methyl formate, in the presence of bases, such as, for example, sodium methylate, and, if appropriate, with the use of diluents, such as, for example, methanol, at temperatures between 0° and 50° C., and reacting the resulting products with amidines of the formula (VIII) or their hydrochlorides, such as, for example, methylthio-propionamidine hydrochloride, likewise at temperatures between 0° and 50° C. To work up the mixture, the solvent is stripped off in vacuo, the residue is dissolved in water, and the pH value is adjusted to about 6. The solution is extracted with a water-immiscible solvent, such as, for example, methylene chloride, and the solvent is distilled off from the extract, the product being obtained as a solid or oily residue. Alkylthioalkylene-hydroxy-pyrimidines of the formula (II) can be oxidized with oxidizing agents, such as, for example, hydrogen peroxide or 3-chloro-perbenzoic acid, at temperatures between 0° and 50° C., if appropriate with the use of diluents, such as, for example, acetic acid or chloroform, to give the corresponding alkylsulphinyl- or alkylsulphonyl-alkylene-hydroxy-pyrimidines.

N,N-Dimethyl-carbamic acid chloride may be mentioned as an example of the carbamic acid halides of the formula (III) which are to be used in process (a). This compound, and the reactants phosgene and dimethylamine which are to be employed in process (b), are known.

Formula (I) gives a definition of the compounds to be used as starting materials in process (c). In this formula, R, $R^2$ and A preferably have those meanings which have been mentioned in the definition of these radicals in formula (I) as being preferred; n represents 0 and/or $R^1$ represents alkylthio having 1 to 6 carbon atoms.

The oxidizing agents to be employed in process (c) are hydrogen peroxide, sodium periodate, nitric acid, halogens, such as chlorine or a hypochlorite, permanganates, such as potassium permanganate, and per-acids, such as perbenzoic acid or chloroperbenzoic acid.

In the case in which compounds of the formula I in which n represents 1 are to be obtained, preferred oxidizing agents are $H_2O_2$ or $H_2O_2$/glacial acetic acid, sodium periodate, nitric acid and halogens. The oxidizing agent is added in a molar ratio of about 1:1 to the compounds of the formula I in which n is 0.

In the case in which compounds of the formula I in which n represents 2 are to be obtained, preferred oxidizing agents are $H_2O_2$ with strong acids, such as $H_2SO_4$, or formic acid, nitric acid, a hypochlorite, permanganates, such as potassium permanganate, per-acids, such as perbenzoic acid or chloroperbenzoic acid. The oxidizing agent is added in a molar ratio of about 2:1 to the compounds of the formula I in which n is 0.

Formula (IV) gives a general definition of the N,N-dimethyl O-pyrimidin-4-yl carbamates to be used as starting materials in process (d). In this formula, R, $R^1$, $R^2$ and n preferably have those meanings which have been mentioned in the definition of these radicals or indices in formula (I) as being preferred.

The following may be mentioned as an example of the compounds of the formula (IV):

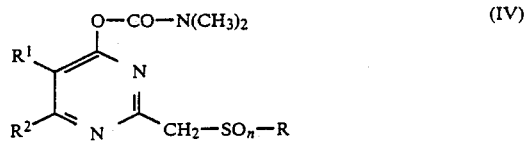

(IV)

TABLE 2

| $R^1$ | $R^2$ | R | n |
|---|---|---|---|
| CH$_3$ | CH$_3$ | CH$_3$ | 0 |
| CH$_3$ | CH$_3$ | CH$_3$ | 1 |

TABLE 2-continued

| $R^1$ | $R^2$ | R | n |
|---|---|---|---|
| CH$_3$ | CH$_3$ | CH$_3$ | 2 |
| —CH$_2$—CH$_2$—CH$_2$— | | CH$_3$ | 0 |
| —CH$_2$—CH$_2$—CH$_2$— | | CH$_3$ | 1 |
| —CH$_2$—CH$_2$—CH$_2$— | | CH$_3$ | 2 |
| —OCH$_3$ | H | CH$_3$ | 0 |
| —OCH$_3$ | H | CH$_3$ | 1 |
| —OCH$_3$ | H | CH$_3$ | 2 |
| —OC$_2$H$_5$ | H | CH$_3$ | 0 |
| —OC$_2$H$_5$ | H | CH$_3$ | 1 |
| —OC$_2$H$_5$ | H | CH$_3$ | 2 |
| —O—i-C$_3$H$_7$ | H | CH$_3$ | 0 |
| CH$_3$ | CH$_3$ | C$_2$H$_5$ | 0 |
| CH$_3$ | CH$_3$ | C$_2$H$_5$ | 1 |
| CH$_3$ | CH$_3$ | C$_2$H$_5$ | 2 |
| —OCH$_3$ | H | C$_2$H$_5$ | 0 |
| —OCH$_3$ | H | C$_2$H$_5$ | 1 |
| —OCH$_3$ | H | C$_2$H$_5$ | 2 |
| —OCH$_3$ | H | n-C$_3$H$_7$ | 0 |
| —OCH$_3$ | H | n-C$_3$H$_7$ | 1 |
| —OCH$_3$ | H | n-C$_3$H$_7$ | 2 |
| —OCH$_3$ | H | tert.—C$_4$H$_9$ | 0 |
| —OCH$_3$ | H | tert.—C$_4$H$_9$ | 1 |
| —OCH$_3$ | H | tert.—C$_4$H$_9$ | 2 |
| CH$_3$ | H | CH$_3$ | 0 |
| CH$_3$ | H | CH$_3$ | 1 |
| CH$_3$ | H | CH$_3$ | 2 |
| C$_2$H$_5$ | H | CH$_3$ | 0 |
| C$_2$H$_5$ | H | CH$_3$ | 1 |
| C$_2$H$_5$ | H | CH$_3$ | 2 |
| n-C$_3$H$_7$ | H | CH$_3$ | 0 |
| n-C$_3$H$_7$ | H | CH$_3$ | 1 |
| n-C$_3$H$_7$ | H | CH$_3$ | 2 |
| i-C$_3$H$_7$ | H | CH$_3$ | 0 |
| i-C$_3$H$_7$ | H | CH$_3$ | 1 |
| i-C$_3$H$_7$ | H | CH$_3$ | 2 |
| i-C$_3$H$_7$ | H | CH$_3$ | 3 |
| H | CH$_3$ | CH$_3$ | 0 |
| H | CH$_3$ | CH$_3$ | 1 |
| H | CH$_3$ | CH$_3$ | 2 |
| —SCH$_3$ | H | CH$_3$ | 0 |
| —SCH$_3$ | H | CH$_3$ | 1 |
| —SCH$_3$ | H | CH$_3$ | 2 |
| H | tert.—C$_4$H$_9$ | CH$_3$ | 0 |
| H | n-C$_4$H$_9$ | CH$_3$ | 0 |
| H | i-C$_4$H$_9$ | CH$_3$ | 0 |
| —SCH$_3$ | C$_2$H$_5$ | CH$_3$ | 0 |
| OC$_2$H$_5$ | H | C$_2$H$_5$ | 0 |

The compounds of the formula (IV) are known (in this context, see U.S. Pat. Nos. 4,323,571 and 4,234,587, or can be prepared in a simple manner by the processes described in these publications.

Formula (V) gives a general definition of the alkyl halides furthermore to be used as starting materials in process (d). In this formula, $R^3$ preferably represents $C_1$-$C_5$-alkyl and Hal preferably represents chlorine, bromine or iodine.

The following may be mentioned as an example of the compounds of the formula (V): methyl, ethyl, n-propyl, i-propyl, n-butyl, i-butyl, sec.-butyl, tert.-butyl, n-pentyl, 2-pentyl, 3-pentyl, 2-methyl-but-1-yl, 2-methyl-but-2-yl, 2-methyl-but-3-yl, 2-methyl-but-4-yl or 2,2-dimethyl-prop-1-yl chloride or bromide or iodide.

The compounds of the formula (V) are generally known compounds of organic chemistry.

The processes (a) to (d) for the preparation of the new substituted N,N-dimethyl O-pyrimidin-4-yl carbamates are carried out in general using diluents.

Suitable diluents are virtually all inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethyl acetamide and N-methylpyrrolidone, and dimethylsulphoxide, tetramethylenesulphone and hexamethylphosphoric acid triamide.

If hydrogen peroxide is employed as the oxidizing agent in process (c), preferred diluents are aliphatic carboxylic acids, such as, for example, formic acid, acetic acid or propionic acid.

Processes (a), (b) and (d) are carried out in general using acid acceptors. All customary acid-binding agents can be used as acid acceptors. Alkali metal carbonates and alkali metal alcoholates, such as sodium carbonate and potassium carbonate, and sodium methylate, potassium methylate, sodium ethylate, potassium ethylate and potassium tert.-butylate, and also aliphatic, aromatic or heterocyclic amines, for example triethylamine, trimethylamine, dimethyl-aniline, dimethylbenzylamine, pyridine, diazabicyclooctane, diazabicyclononane and diazabicycloundecene, have proved particularly suitable.

The processes according to the invention are carried out in general at temperatures between 0° and 150° C. The temperature range between 20° and 100° C. is preferred for process (a), and the range between 0° and 50° C. is preferred for processes (b), (c) and (d). The reactions are carried out in general under atmospheric pressure.

To carry out process (a) or (b), between 1.0 and 1.3, preferably between 1.0 and 1.15, mols of N,N-dimethylcarbamic acid chloride, or phosgene and dimethylamine, respectively, are employed per mol of hydroxypyrimidine of the formula (II). The reaction is carried out in general in a diluent, in the presence of an acid acceptor. After the reaction is complete, the mixture is filtered and the solvent is distilled off in vacuo.

In process (c), between 1 and 3 mols of oxidising agent are employed per mol of the compound of the formula (I). The reaction is carried out in general in a diluent. After the reaction is complete, the solution is washed, dried and filtered, and the solvent is distilled off in vacuo.

To carry out process (d), between 1.0 and 1.3, preferably between 1.0 and 1.15, mols of alkyl halide of the formula (V) are employed per mol of N,N-dimethyl O-pyrimidin-4-yl carbamate of the formula (IV). The reaction is carried out in general in a diluent, in the presence of an acid acceptor.

The new compounds are obtained in the form of oils, which in some cases cannot be distilled without decomposition, but are freed from the last volatile constituents by so-called "incipient distillation", that is to say, by prolonged heating to moderately elevated temperatures under reduced pressure, and are purified in this manner. They are characterized by the refractive index.

If the new compounds are obtained in solid form after the solvent has been distilled off, they are purified by recrystallization. They are characterized by the melting point.

Substituted N,N-dimethyl O-pyrimidin-4-yl carbamates according to the invention are distinguished by high insecticidal activity, in particular also systemic and root-systemic activity.

The active compounds are well tolerated by plants, have a favorable level of toxicity to warm-blooded animals, and are suitable for combating animal pests, especially insects, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp. *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Tineola bisseliella* and *Tinea pellionella.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaeophilus surinamensis,* Anthronomus spp., Sitophilus spp., *Otiorrhynchus sulcatus,*

*Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations, and in the use forms, prepared from these formulations, as a mixture with other active compounds, such as insecticides, baits, a sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of livestock husbandry and livestock breeding, it being possible to achieve better results, for example higher milk outputs, higher weight, longer life span, etcetera, by combating pests.

The active compounds according to the invention are used in a known manner in these fields, such as by oral administration, for example in the form of tablets, capsules, drinks and granules, by dermal application, for example in the form of dipping, spraying, pouring on and spotting on, and dusting, and by parenteral administration, for example in the form of an injection.

PREPARATION EXAMPLES

EXAMPLE 1

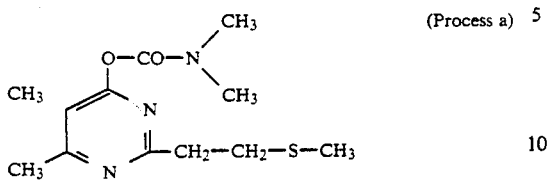
(Process a)

A mixture of 39.6 g (0.2 mol) of 2-(2-methylthioethyl)-4-hydroxy-5,6-dimethylpyrimidine, 41.4 g (0.3 mol) of potassium carbonate, 300 ml of acetonitrile and 21.5 g (0.2 mol) of dimethylcarbamic acid chloride is stirred for 48 hours at 60° C. The solution is then filtered off from undissolved materials and rinsed with acetonitrile, and the filtrate is evaporated down in vacuo. The residue is subjected to incipient distillation at 60° C., in a high vacuum. 49 g (91% of theory) of N,N-dimethyl O-(2-(2-methylthio-ethyl)-5,6-dimethylpyrimidin-4-yl)carbamate are obtained in this manner in the form of a brown oil having a refractive index $n_D^{20}$: 1.5350.

EXAMPLE 2

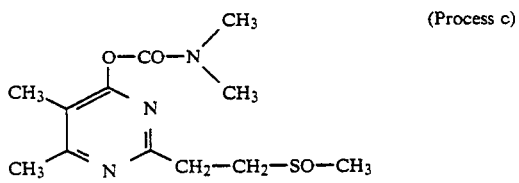
(Process c)

5.7 g of a 30% strength solution of hydrogen peroxide are added dropwise to a solution of 13.4 g (0.05 mol) of N,N-dimethyl O-(2-(2-methylthio-ethyl)-5,6-dimethyl-pyrimidin-4-yl)carbamate in 100 ml of glacial acetic acid at 10° C. The mixture is stirred for a further 20 hours without cooling, and a 40% strength sodium bisulphite solution is then added until all peroxide is destroyed. The solution is then evaporated down in vacuo, the residue is dissolved in 100 ml of methylene chloride, and the solution is extracted once by shaking with 25 ml of 30% strength potassium carbonate solution. The organic phase is dried over sodium sulphate and evaporated down in vacuo. After incipient distillation, 13.8 g (88% of theory) of N,N-dimethyl O-(2-(2-methylsulphinyl-ethyl)-5,6-dimethyl-pyrimidin-4-yl)carbamate are obtained as a yellow oil having a refractice index $n_D^{20}$: 1.5372.

EXAMPLE 3

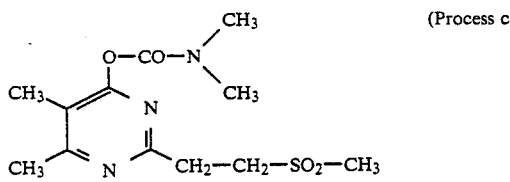
(Process c)

A solution of 22.3 g (0.13 mol) of 3-chloroperoxybenzoic acid in 200 ml of chloroform is added to a solution of 13.4 g (0.05 mol) of N,N-dimethyl O-(2-(2-methylthio-ethyl)-5,6-dimethyl-pyrimidin-4-yl)carbamate in 50 ml of chloroform, while cooling at 5°-10° C. The reaction mixture is stirred for a further 18 hours without cooling, and then filtered. The filtrate is then extracted once by shaking with 15 ml of a 30% strength potassium carbonate solution, the organic phase is dried over sodium sulphate, and the solvent is then distilled off in vacuo. 12 g (73% of theory) of N,N-dimethyl O-(2-(2-methyl-sulphonyl-ethyl)-5,6-dimethyl-pyrimidin-4-yl)carbamate in the form of colorless crystals with a melting point of 98° C. remain.

EXAMPLE 4

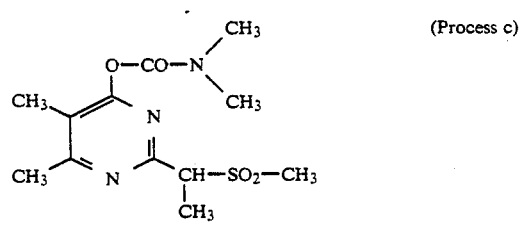
(Process c)

24.2 g of 30% strength hydrogen peroxide solution are added dropwise to a solution of 20.2 g (0.075 mol) of N,N-dimethyl O-(2-(1-methylthio-ethyl)-5,6-dimethyl-pyrimidin-4-yl)carbamate in a mixture of 150 ml of methylene chloride, 7.5 g of formic acid and 0.8 g of concentrated sulphuric acid. The reaction temperature increases to about 40° C. The mixture is then stirred for a further 18 hours without cooling, 40% strength sodium bisulphite solution is added until the unreacted peroxide has been destroyed, and the mixture is then extracted by shaking with 50 ml of 30% strength potassium carbonate solution. The organic phase is dried over sodium sulphate and evaporated down in vacuo. 19 g (84% of theory) of N,N-dimethyl O-(2-(1-methyl-sulphonylethyl)-5,6-dimethyl-pyrimidin-4-yl)carbamate are obtained in this manner in the form of colorless crystals having a melting point of 128° C.

EXAMPLE 5

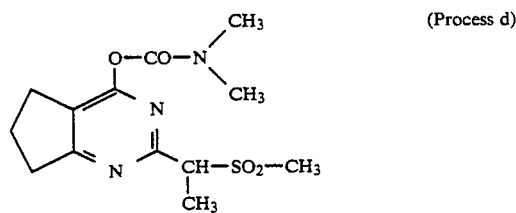
(Process d)

15 g (0.05 mol) of N,N-dimethyl O-(2-methylsulphonylmethyl-5,6-trimethylene-pyrimidin-4-yl)carbamate, and thereafter 7.8 g (0.055 mol) of methyl iodide, are added to a solution of 5.8 g (0.052 mol) of potassium tert. butylate in 200 ml of tetrahydrofuran at 20°-25° C., and the mixture is stirred for a further 18 hours at 20°-25° C. 500 ml of toluene are then added, and the mixture is extracted by shaking with twice 100 ml of water. The organic phase is dried over sodium sulphate and evaporated down in vacuo. 9.5 g (64% of theory) of N,N-dimethyl O-(2-(1-methylsulphonyl-ethyl)-5,6-trimethylene-pyrimidin-4-yl)carbamate in the form of beige crystals with a melting point of 92° C. remain.

The following compounds of the formula

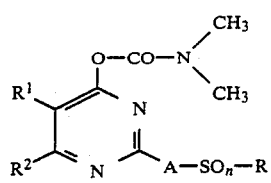

(I)

can be prepared analogously to one of the Examples 1 to 5:

| Example No. | R | R¹ | R² | A | n | Melting point [°C.]; refractive index |
|---|---|---|---|---|---|---|
| 6 | $CH_3$ | —$CH_2$—$CH_2$—$CH_2$— | | —CH—<br>\|<br>$C_2H_5$ | 2 | 136 |
| 7 | $CH_3$ | —$CH_2$—$CH_2$—$CH_2$— | | —$CH_2$—$CH_2$— | 0 | $n_D^{20}$: 1.5490 |
| 8 | $CH_3$ | $CH_3O$ | H | —$CH_2$—$CH_2$— | 0 | 44 |
| 9 | $CH_3$ | $CH_3$ | $CH_3$ | —CH—<br>\|<br>$CH_3$ | 0 | 40 |
| 10 | $CH_3$ | $CH_3O$ | H | —CH—<br>\|<br>$CH_3$ | 0 | 112 |
| 11 | $CH_3$ | —$CH_2$—$CH_2$—$CH_2$— | | —CH—<br>\|<br>$CH_3$ | 0 | 39 |
| 12 | $CH_3$ | $CH_3$ | $CH_3$ | —CH—<br>\|<br>$CH_3$ | 1 | $n_D^{22}$: 1.5362 |
| 13 | $CH_3$ | $CH_3O$ | H | —CH—<br>\|<br>$CH_3$ | 1 | 127 |
| 14 | $CH_3$ | $CH_3O$ | H | —CH—<br>\|<br>$CH_3$ | 2 | 144 |
| 15 | $CH_3$ | —$CH_2$—$CH_2$—$CH_2$— | | —CH—<br>\|<br>$CH_3$ | 1 | 71 |
| 16 | $CH_3$ | $C_2H_5O$ | H | —CH—<br>\|<br>$CH_3$ | 0 | $n_D^{21}$: 1.5357 |
| 17 | $CH_3$ | $C_2H_5O$ | H | —CH—<br>\|<br>$CH_3$ | 1 | 68 |
| 18 | $CH_3$ | $C_2H_5O$ | H | —CH—<br>\|<br>$CH_3$ | 2 | 84 |
| 19 | $CH_3$ | $CH_3O$ | H | —$CH_2$—$CH_2$— | 1 | |
| 20 | $CH_3$ | $CH_3O$ | H | —$CH_2$—$CH_2$— | 2 | |
| 21 | $CH_3$ | $C_2H_5O$ | H | —$CH_2$—$CH_2$— | 0 | |
| 22 | $CH_3$ | i-$C_3H_7O$ | H | —$CH_2$—$CH_2$— | 0 | |
| 23 | $C_2H_5$ | $CH_3$ | $CH_3$ | —$CH_2$—$CH_2$— | 0 | |
| 24 | $C_2H_5$ | $CH_3O$ | H | —$CH_2$—$CH_2$— | 0 | |
| 25 | n-$C_3H_7$ | $CH_3$ | $CH_3$ | —$CH_2$—$CH_2$— | 0 | |
| 26 | n-$C_3H_7$ | $CH_3O$ | H | —$CH_2$—$CH_2$— | 0 | |
| 27 | tert.-$C_4H_9$ | $CH_3$ | $CH_3$ | —$CH_2$—$CH_2$— | 0 | |
| 28 | tert.$C_4H_9$ | $CH_3O$ | H | —$CH_2$—$CH_2$— | 0 | |
| 29 | $CH_3$ | $CH_3O$ | H | —$CH_2$—$CH_2$—$CH_2$— | 0 | 28 |
| 30 | $CH_3$ | $CH_3O$ | H | —$CH_2$—$CH_2$—$CH_2$— | 1 | 100 |
| 31 | $CH_3$ | $CH_3O$ | H | —$CH_2$—$CH_2$—$CH_2$— | 2 | 118 |
| 32 | $CH_3$ | $CH_3$ | $CH_3$ | —$CH_2$—$CH_2$—$CH_2$— | 0 | $n_D^{20}$: 1.5317 |
| 33 | $CH_3$ | $CH_3$ | H | —$CH_2$—$CH_2$— | 0 | |

-continued

| Example No. | R | R¹ | R² | A | n | Melting point [°C.]; refractive index |
|---|---|---|---|---|---|---|
| 34 | $CH_3$ | $CH_3$ | H | $-CH-$<br>$\;\;\;\|$<br>$\;\;CH_3$ | 0 | |
| 35 | $CH_3$ | $C_2H_5$ | H | $-CH_2-CH_2-$ | 0 | |
| 36 | $CH_3$ | $C_2H_5$ | H | $-CH-$<br>$\;\;\;\|$<br>$\;\;CH_3$ | 0 | |
| 37 | $CH_3$ | $i\text{-}C_3H_7$ | H | $-CH_2-CH_2-$ | 0 | |
| 38 | $CH_3$ | $i\text{-}C_3H_7$ | H | $-CH-$<br>$\;\;\;\|$<br>$\;\;CH_3$ | 0 | |
| 40 | $CH_3$ | H | $CH_3$ | $-CH_2-CH_2-$ | 0 | |
| 41 | $CH_3$ | $C_2H_5O$ | H | $-CH_2-CH_2-$ | 1 | |
| 42 | $CH_3$ | $C_2H_5O$ | H | $-CH_2-CH_2-$ | 2 | |
| 43 | $CH_3$ | $CH_3S$ | H | $-CH_2-CH_2-$ | 0 | |
| 44 | $CH_3$ | $CH_3S$ | H | $-CH-$<br>$\;\;\;\|$<br>$\;\;CH_3$ | 0 | |
| 45 | $CH_3$ | $CH_3O$ | H | $\;\;\;CH_3$<br>$\;\;\;\|$<br>$-C-CH_2-$<br>$\;\;\;\|$<br>$\;\;\;CH_3$ | 0 | |
| 46 | $CH_3$ | $CH_3$ | $CH_3$ | $\;\;\;CH_3$<br>$\;\;\;\|$<br>$-C-CH_2-$<br>$\;\;\;\|$<br>$\;\;\;CH_3$ | 0 | |
| 47 | $CH_3$ | $CH_3O$ | H | $\;\;\;CH_3$<br>$\;\;\;\|$<br>$-C-$<br>$\;\;\;\|$<br>$\;\;\;CH_3$ | 0 | |
| 48 | $CH_3$ | $CH_3$ | $CH_3$ | $\;\;\;CH_3$<br>$\;\;\;\|$<br>$-C-$<br>$\;\;\;\|$<br>$\;\;\;CH_3$ | 0 | |
| 49 | $CH_3$ | $CH_3O$ | H | $\;\;\;CH_3$<br>$\;\;\;\|$<br>$-C-$<br>$\;\;\;\|$<br>$\;\;\;CH_3$ | 1 | |
| 50 | $CH_3$ | $CH_3O$ | H | $\;\;\;CH_3$<br>$\;\;\;\|$<br>$-C-$<br>$\;\;\;\|$<br>$\;\;\;CH_3$ | 2 | |
| 51 | $CH_3$ | $CH_3$ | $CH_3$ | $\;\;\;CH_3$<br>$\;\;\;\|$<br>$-C-$<br>$\;\;\;\|$<br>$\;\;\;CH_3$ | 1 | |
| 52 | $CH_3$ | $CH_3$ | $CH_3$ | $\;\;\;CH_3$<br>$\;\;\;\|$<br>$-C-$<br>$\;\;\;\|$<br>$\;\;\;CH_3$ | 2 | |
| 53 | $CH_3$ | $CH_3$ | H | $-CH-CH_2-$<br>$\;\;\|$<br>$\;CH_3$ | 0 | |
| 54 | $CH_3$ | $CH_3$ | $CH_3$ | $-CH-CH_2-$<br>$\;\;\|$<br>$\;CH_3$ | 0 | |

| Example No. | R | R¹ | R² | A | n | Melting point [°C.]; refractive index |
|---|---|---|---|---|---|---|
| 55 | CH₃ | H | t.-C₄H₉ | —CH₂—CH₂— | 0 | |

PRECURSORS

The substituted hydroxy-pyrimidines of the formula (II) which are to be used as starting materials can be prepared, for example, as follows:

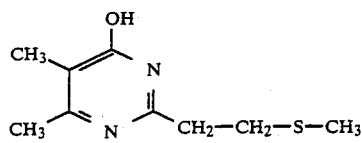

First 77.3 g (0.5 mol) of 3-methylthiopropionamidine hydrochloride and then 100.7 g (0.5 mol) of 71.4% strength ethyl 2-methylacetoacetate are added to a solution of 54 g (1 mol) of sodium methanolate in 300 ml of methanol. During this procedure, the reaction temperature increases to approx. 35° C. The mixture is then stirred for a further 4 hours, and the solvent is distilled off in vacuo. The residue is dissolved in 800 ml of warm water, and the solution is adjusted to pH 6 by the addition of concentrated hydrochloric acid. After the solution has been cooled to 5° C., the precipitated product is filtered off under suction. 66 g (67% of theory) of 2-(2-methylthio-)ethyl-4-hydroxy-5,6-dimethylpyrimidine are obtained in this manner in the form of a colorless powder with a melting point of 120° C.

The following compounds of the formula

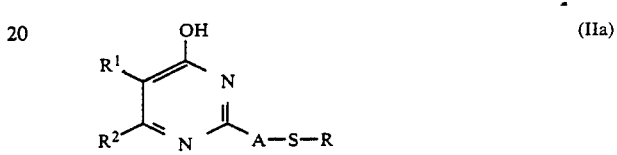

can be prepared analogously:

| R | R¹ | R² | A | Melting point [°C.] |
|---|---|---|---|---|
| CH₃ | —CH₂—CH₂—CH₂— | | —CH₂—CH₂— | 164 |
| CH₃ | CH₃O | H | —CH₂—CH₂— | 155 |
| CH₃ | CH₃ | CH₃ | —CH—<br>\|<br>CH₃ | 89 |
| CH₃ | CH₃O | H | —CH—<br>\|<br>CH₃ | 149 |
| CH₃ | —CH₂—CH₂—CH₂— | | —CH—<br>\|<br>CH₃ | 154 |
| CH₃ | C₂H₅O | H | —CH—<br>\|<br>CH₃ | 129 |
| CH₃ | C₂H₅O | H | —CH₂—CH₂— | |
| CH₃ | i-C₃H₇O | H | —CH₂—CH₂— | |
| C₂H₅ | CH₃ | CH₃ | —CH₂—CH₂— | |
| C₂H₅ | CH₃O | H | —CH₂—CH₂— | |
| n-C₃H₇ | CH₃ | CH₃ | —CH₂—CH₂— | |
| n-C₃H₇ | CH₃O | H | —CH₂—CH₂— | |
| tert.-C₄H₉ | CH₃ | CH₃ | —CH₂—CH₂— | |
| tert.-C₄H₉ | CH₃O | H | —CH₂—CH₂— | |
| CH₃ | CH₃O | H | —CH₂—CH₂—CH₂— | 137 |
| CH₃ | CH₃ | CH₃ | —CH₂—CH₂—CH₂— | 102 |
| CH₃ | CH₃ | H | —CH₂—CH₂— | |
| CH₃ | CH₃ | H | —CH—<br>\|<br>CH₃ | |
| CH₃ | C₂H₅ | H | —CH₂—CH₂— | |
| CH₃ | C₂H₅ | H | —CH—<br>\|<br>CH₃ | |
| CH₃ | i-C₃H₇ | H | —CH₂—CH₂— | |
| CH₃ | i-C₃H₇ | H | —CH—<br>\|<br>CH₃ | |

-continued

| R | R¹ | R² | A | Melting point [°C.] |
|---|---|---|---|---|
| CH₃ | H | CH₃ | —CH₂—CH₂— | |
| CH₃ | CH₃S | H | —CH₂—CH₂— | |
| CH₃ | CH₃S | H | —CH(CH₃)— | |
| CH₃ | CH₃O | H | —C(CH₃)₂—CH₂— | |
| CH₃ | CH₃ | CH₃ | —C(CH₃)₂—CH₂— | |
| CH₃ | CH₃O | H | —C(CH₃)₂— | |
| CH₃ | CH₃ | CH₃ | —C(CH₃)₂— | |
| CH₃ | CH₃O | H | —CH(CH₃)—CH₂— | |
| CH₃ | CH₃ | CH₃ | —CH(CH₃)—CH₂— | |
| CH₃ | H | t.-C₄H₉ | —CH₂—CH₂— | |

USE EXAMPLES

The following compounds are employed as comparative substances in the examples which follow:

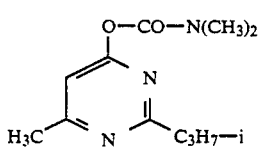

N,N-Dimethyl O-(2-iso-propyl-6-methyl-pyrimidin-4-yl)carbamate (French Patent Specification No. 1,443,910)

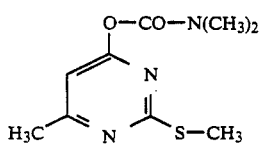

N,N-Dimethyl O-(2-methylthio-6-methyl-pyrimidin-4-yl)carbamate (U.S. Pat. No. 2,694,712)

EXAMPLE A

Doralis test (systemic action)

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia fabae*) which have been heavily infested with the bean aphid (*Doralis fabae*) are each watered with 20 ml of the preparation of the active compound of the desired concentration in such a way that the preparation of the active compound penetrates into the soil without wetting the shoot. The active compound is taken up by the roots and passes to the shoot.

After the specified periods of time, the destruction in % is determined. 100% means that all the aphids have been killed; 0% means that none of the aphids have been killed.

In this test, for example, the following compounds from the preparation examples show a superior activity compared to the prior art: (10), (9), (11), (13), (12), (17), (15), (14), (5), (4), (6), (8), (1), (7), (2) and (3).

EXAMPLE B

Root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l) being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test animals have been killed and 0% if just as many test insects are still alive as in the case of the untreated control.

In this test, for example, the following compounds from the preparation examples show a superior action compared to the prior art: (5), (6), (1), (7), (2), (3), (8), (9), (10), (11), (12), (4), (13), (14), (15), (16), (17) and (18).

EXAMPLE C

Test with *Lucilia cuprina* res. larvae
Emulsifier: 35 parts by weight of ethylene glycol monomethyl ether; 35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains about 1 cm² of horse muscle and 0.5 ml of the preparation of active compound. After 24 hours, the degree of destruction is determined.

In this test, for example, the compound of Example (5) showed a destruction of 100% at an active compound concentration of 1,000 ppm.

It will be understood that the specification and examples are illustrative but not limitative of the present invention and that other embodiments within the spirit and scope of the invention will suggest themselves to those skilled in the art.

We claim:

1. A substituted N,N-dimethyl O-pyrimidin-4-ylcarbamate of the formula

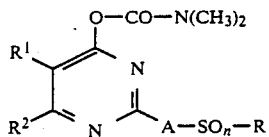

in which

R is alkyl having 1 to 6 carbon atoms,
$R^1$ is hydrogen, or alkyl, alkoxy, alkylthio, alkylsulphinyl or alkylsulphonyl, each of which has 1 to 6 carbon atoms and is optionally substituted by halogen, $C_{1-2}$-alkoxy or $C_{1-2}$-alkylthio,
$R^2$ is hydrogen, or alkyl which has 1 to 6 carbon atoms and is optionally substituted by halogen, $C_{1-2}$-alkoxy or $C_{1-2}$-alkylthio, or
$R^1$ and $R^2$ together form alkylene which has 2 to 4 carbon atoms and is optionally substituted by halogen, $C_{1-2}$-alkyl or $C_{1-2}$-alkylthio, and alkylene having 2 to 6 atoms,
A is alkylene having 2 to 6 carbon atoms, and
n is 0, 1 or 2.

2. A compound according to claim 1, in which
R is methyl, ethyl, n-propyl, i-propyl, n-butyl, i-butyl, sec.-butyl or tert.-butyl,
$R^1$ is hydrogen, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, n-propylthio, i-propylthio, n-butylthio, i-butylthio, sec.-butylthio, tert.-butylthio, or methyl-, ethyl-, n-propyl-, i-propyl-, n-butyl-, i-butyl-, sec.-butyl- or tert.-butyl-sulphinyl or -sulphonyl,
$R^2$ is hydrogen, methyl, ethyl, n-propyl, i-propyl, n-butyl, i-butyl, sec.-butyl or tert.-butyl, or
$R^1$ and $R^2$ together form alkylene having 2 to 4 carbon atoms, and
A is alkylene having 2 to 6 carbon atoms and
n is 0, 1 or 2.

3. A compound according to claim 1, wherein such compound is N,N-dimethyl O-(2-(2-methylsulphinyl-ethyl)-5,6-dimethyl-pyrimidin-4-yl)carbamate of the formula

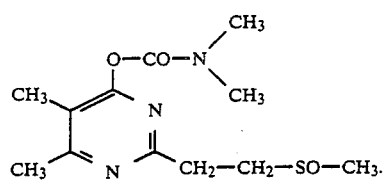

4. A compound according to claim 1, wherein such compound is N,N-dimethyl O-(2-(1-methylsulphonyl-ethyl)-5,6-dimethyl-pyrimidin-4-yl)carbamate of the formula

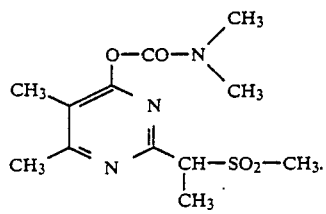

5. A compound according to claim 1, wherein such compound is N,N-dimethyl O-(2-(2-methylthio-ethyl)-5-methoxy-pyrimidin-4-yl)carbamate of the formula

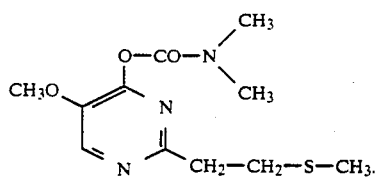

6. A compound according to claim 1, wherein such compound is N,N-dimethyl O-(2-(1-methylthio-ethyl)-5,6-trimethylene-pyrimidin-4-yl)carbamate of the formula

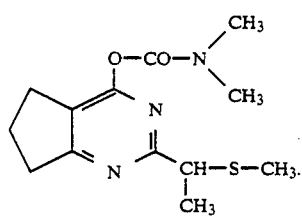

7. A compound according to claim 1, wherein such compound is N,N-dimethyl O-(2-(1-methylsulphinyl-ethyl)-5-methoxy-pyrimidin-4-yl)carbamate of the formula

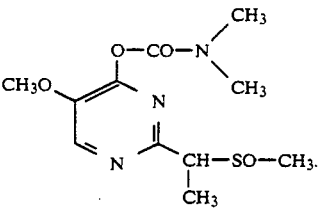

8. An insecticidal composition comprising an insecticidally effective amount of a compound according to claim 1 in admixture with a diluent.

9. A method of combating insects which comprises applying to such insects or an insect habitat an insecticidally effective amount of a compound according to claim 1.

10. The method according to claim 9, wherein such compound is
N,N-dimethyl O-(2-(2-methylsulphinyl-ethyl)-5,6-dimethyl-pyrimidin-4-yl)carbamate,
N,N-dimethyl O-(2-(1-methylsulphonyl-ethyl)-5,6-dimethyl-pyrimidin-4-yl)carbamate,
N,N-dimethyl O-(2-(2-methylthio-ethyl)-5-methoxypyrimidin-4-yl)carbamate,
N,N-dimethyl O-(2-(1-methylthio-ethyl)-5,6-trimethylene-pyrimidin-4-yl)carbamate or
N,N-dimethyl O-(2-(1-methylsulphinyl-ethyl)-5-methoxy-pyrimidin-4-yl)carbamate.

* * * * *

UNITED STATES PATENT AND TRADEMARK OFFICE
CERTIFICATE OF CORRECTION

PATENT NO. : 4,503,057

DATED : March 5, 1985

INVENTOR(S) : Fritz Maurer, et al

It is certified that error appears in the above-identified patent and that said Letters Patent is hereby corrected as shown below:

Col. 10, lines 67, 68      Correct spelling of "Anthonomus"

Col. 13, line 7      Delete beginning of formula and substitute

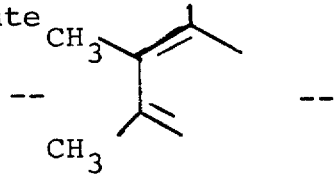

Col. 13, lines 51, 52      Correct spelling of "refractive"

Col. 17, Example 53, under "$R^1$"      Delete "$CH_3$" and substitute --$CH_3O$--

Col. 23, line 58      After "yl" insert a space

Col. 26, lines 24, 25      After "methoxy" insert -- - --

Signed and Sealed this

Sixth Day of August 1985

[SEAL]

Attest:

DONALD J. QUIGG

Attesting Officer      Acting Commissioner of Patents and Trademarks